(12) United States Patent
Skreosen

(10) Patent No.: US 9,125,758 B2
(45) Date of Patent: Sep. 8, 2015

(54) FLUID ABSORBING SHEET

(75) Inventor: Astrid Skreosen, Brevik (NO)

(73) Assignee: ASAP-NORWAY AS, Skien (NO)

( * ) Notice: Subject to any disclaimer, the term of this patent is extended or adjusted under 35 U.S.C. 154(b) by 271 days.

(21) Appl. No.: 13/057,240

(22) PCT Filed: Aug. 4, 2009

(86) PCT No.: PCT/EP2009/060100
§ 371 (c)(1),
(2), (4) Date: Apr. 26, 2011

(87) PCT Pub. No.: WO2010/015630
PCT Pub. Date: Feb. 11, 2010

(65) Prior Publication Data
US 2011/0190720 A1    Aug. 4, 2011

(30) Foreign Application Priority Data
Aug. 4, 2008  (EP) .................................... 08161744

(51) Int. Cl.
*A61F 13/15* (2006.01)
*A61F 5/48* (2006.01)
(Continued)

(52) U.S. Cl.
CPC ............ *A61F 5/485* (2013.01); *A61F 13/15699* (2013.01); *A61F 13/15756* (2013.01); *A61F 13/47* (2013.01); *A61F 13/495* (2013.01); *A61F 13/505* (2013.01); *A61F 13/53* (2013.01); *D04H 1/407* (2013.01); *D04H 13/00* (2013.01);
(Continued)

(58) Field of Classification Search
CPC ......... A61F 5/44; A61F 5/4401; A61F 13/15; A61F 13/47; A61F 13/49; A61F 13/51; A61F 13/53; D04H 1/40; D04H 1/407; D04H 1/492; D04H 1/548; D04H 1/551; D04H 1/559; D04H 1/72; D04H 3/00
USPC ............ 604/331, 356, 358, 317–319, 385.19; 206/390; 5/482, 486, 494
See application file for complete search history.

(56) References Cited

U.S. PATENT DOCUMENTS 4,704,753 A   11/1987 Lunt
4,744,118 A    5/1988 Lunt
(Continued)

FOREIGN PATENT DOCUMENTS

DE        30 02 136 A1    7/1981
EP        0 291 316 A2   11/1988
(Continued)

OTHER PUBLICATIONS

International Preliminary Report on Patentability dated Feb. 8, 2011 for PCT Application No. PCT/EP2009/060100.
(Continued)

*Primary Examiner* — Melanie Hand
(74) *Attorney, Agent, or Firm* — Knobbe Martens Olson & Bear LLP

(57) ABSTRACT

The present invention relates to a fluid absorbing sheet including a bottom- or under-layer of water- or fluid-tight material, a middle layer of super absorbent polymer (SAP) and an upper layer of diffusing material The fluid absorbing sheet may further include at least one water- or fluid-tight bag for collecting and/or disposing of body fluids and/or other body wastes. The invention also relates to a method of manufacturing such a sheet as well as its use.

20 Claims, 13 Drawing Sheets

(51) Int. Cl.
  *A61F 13/47* (2006.01)
  *A61F 13/495* (2006.01)
  *A61F 13/505* (2006.01)
  *A61F 13/53* (2006.01)
  *D04H 1/407* (2012.01)
  *D04H 13/00* (2006.01)

(52) U.S. Cl.
  CPC ............... *A61F2013/53081* (2013.01); *A61F 2013/530547* (2013.01); *Y10T 29/49826* (2015.01); *Y10T 29/49906* (2015.01)

(56) References Cited

U.S. PATENT DOCUMENTS

| | | | |
|---|---|---|---|
| 4,861,632 A | | 8/1989 | Caggiano |
| 4,974,604 A | * | 12/1990 | Morris .................. 128/853 |
| 5,078,705 A | * | 1/1992 | Edwards et al. ............. 604/322 |
| 5,385,105 A | * | 1/1995 | Withers et al. ............... 110/346 |
| 5,618,278 A | * | 4/1997 | Rothrum .................. 604/356 |
| 5,713,372 A | * | 2/1998 | Pinney et al. ............... 128/855 |
| 5,806,114 A | | 9/1998 | Morgan et al. |
| 5,816,709 A | | 10/1998 | Demus |
| 5,820,825 A | | 10/1998 | Weinzierl et al. |
| 6,049,925 A | | 4/2000 | Lewis |
| 6,148,458 A | | 11/2000 | Hires |
| 6,168,019 B1 | * | 1/2001 | Olson ..................... 206/390 |
| 6,179,819 B1 | * | 1/2001 | Haswell .................. 604/356 |
| 6,453,492 B1 | | 9/2002 | Sturrock |
| 6,537,676 B1 | * | 3/2003 | Flynn et al. .................. 428/454 |
| 6,725,479 B1 | | 4/2004 | Stryker et al. |
| 7,086,409 B2 | * | 8/2006 | Robinson .................... 137/1 |
| 7,343,919 B2 | * | 3/2008 | Czajka et al. ............... 128/849 |
| 7,690,380 B2 | * | 4/2010 | Lee et al. ................... 128/853 |
| 7,884,259 B2 | * | 2/2011 | Hanao et al. ................. 604/358 |
| 2002/0128614 A1 | * | 9/2002 | Cinelli et al. ................. 604/332 |
| 2005/0222547 A1 | * | 10/2005 | Beruda et al. ................ 604/368 |
| 2006/0173433 A1 | * | 8/2006 | Laumer et al. ............... 604/372 |
| 2006/0233467 A1 | | 10/2006 | Mize, Jr. |
| 2007/0277323 A1 | * | 12/2007 | Bain et al. ..................... 5/699 |
| 2008/0044607 A1 | * | 2/2008 | Menday et al. ............. 428/36.2 |
| 2008/0154219 A1 | * | 6/2008 | Longo et al. ................. 604/327 |
| 2008/0177252 A1 | * | 7/2008 | Isik ........................... 604/541 |

FOREIGN PATENT DOCUMENTS

| | | |
|---|---|---|
| EP | 0 891 758 A1 | 1/1999 |
| GB | 2 202 738 A | 10/1988 |
| JP | 60-56541 | 4/1985 |
| SE | 519 291 | 2/2003 |
| WO | WO 2006/135562 A2 | 12/2006 |

OTHER PUBLICATIONS

Written Opinion dated Jan. 15, 2010 for PCT Application No. PCT/EP2009/060100.

International Search Report dated Jan. 15, 2010 for PCT Application No. PCT/EP2009/060100.

* cited by examiner

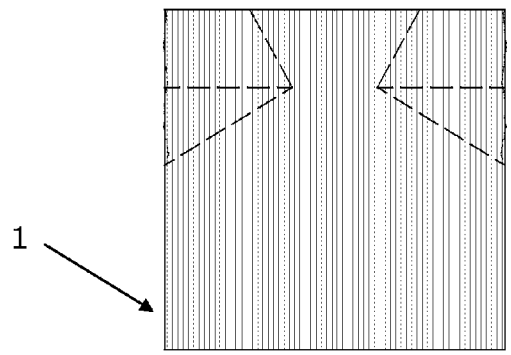
Fig. 9a
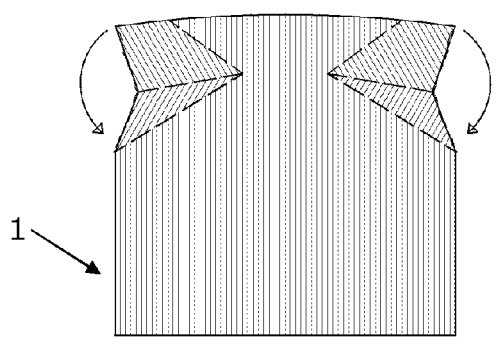
Fig. 9b
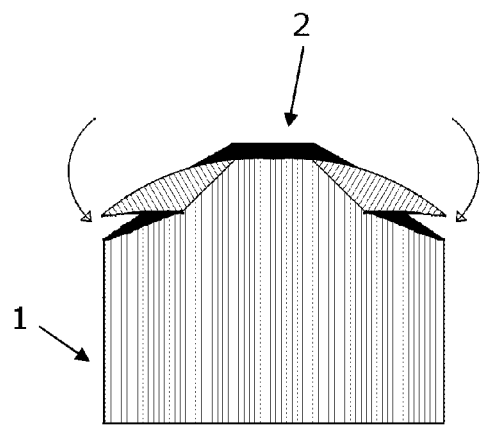
Fig. 9c
Fig. 9

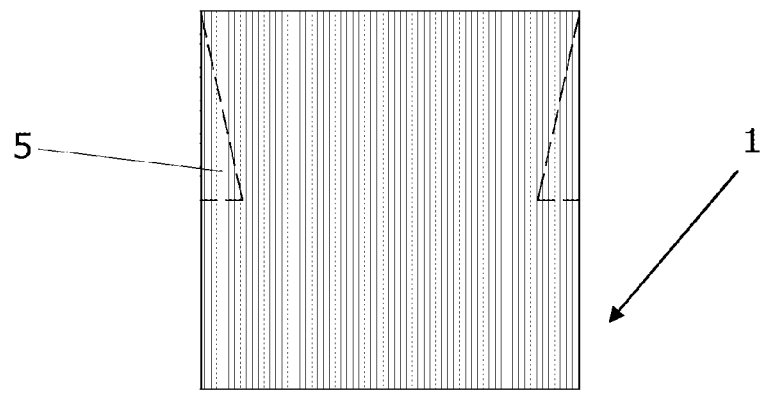
Fig. 10a
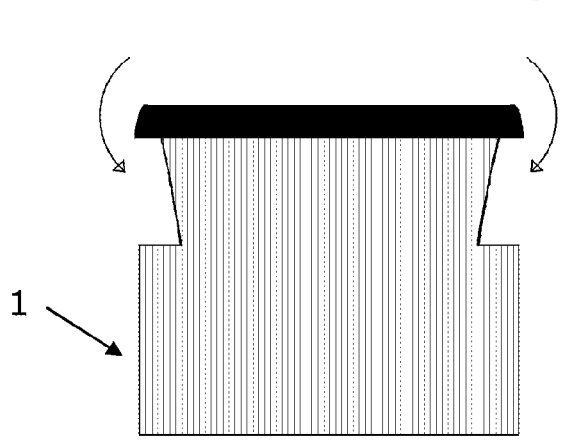
Fig. 10b
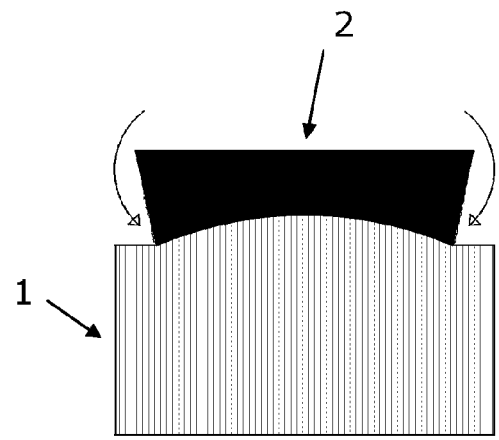
Fig. 10c
Fig. 10

FLUID ABSORBING SHEET

CROSS REFERENCE TO RELATED APPLICATIONS

This application claims the benefit and priority to and is a U.S. National Phase Application of PCT International Application Number PCT/EP2009/060100, filed on Aug. 4, 2009, designating the United States of America and published in the English language, which is an International Application of and claims the benefit of priority to European Patent Application No. 08161744.1, filed on Aug. 4, 2008. The disclosures of the above-referenced applications are hereby expressly incorporated by reference in their entireties.

FIELD OF THE INVENTION

The present invention relates to a fluid absorbing sheet intended for health care or medical related areas of use, such as for example the health, ambulance or nursing services. The invention further relates to a method of manufacturing such a sheet as well as the use of said sheet.

BACKGROUND OF THE INVENTION

Different types of pads and sheet-like articles comprising fluid absorbent materials are used in health or medical related services, such as for example hospitals, ambulances, nursing homes or institutions, etc.

These known pads or sheets have fluid absorbent polymer (s) mixed with filling materials in a layer which is fairly thick, e.g. about 1-2 cm. Examples of such known products are pads from Abena and Tena. As a whole, these known pads or sheets are rather thick and take a lot of storing place.

Other examples of known pads and sheet-like articles are known from e.g. DE 30 02 136 describing an absorbent body comprising: i) a carrier layer, ii) a coating of absorbing, swellable powder and thermoplastic in powder form, and iii) a covering layer. The thermoplastic powder is used both for fixing the absorbing, swellable powder and for merging of the carrier with the covering layer, and a laminating machine or calender bowl is used to fasten the absorbing body together.

EP 0 291 316 relates to an absorbent pad having a densification pattern comprising relatively low density tuft regions which are separated and surrounded by channels. This absorbent pad is positioned between a liquid pervious topsheet and a liquid impervious backsheet. Furthermore, the pad is preferably contained between a pair of tissue layer superposed and subjacent thereto, where the pad and the tissue layer form the absorbent core. The backsheet may be secured to the absorbent core by a uniform continuous layer of adhesive, a patterned layer of adhesive or an array of separate lines or sports of adhesive. The absorbent pad is produced by a densifying apparatus. The absorbent material forms a multiregional "pillow" with several levels of heights due to the densification.

EP 0 891 758 describes a method of making absorbing articles where superabsorbent powder is arranged uniformly between upper and lower sheets. The powder and sheets are compressed in specific areas in order to structurally consolidate the powder in the compressed areas, while the powder in the surrounding areas remains loose. The loose powder located between the compressed zones or areas is extracted by suction or gravity. The regions of the upper and lower sheets are sealed around the periphery of the consolidated areas and furthermore the regions around the consolidated areas are cut. The packet-like article produced comprising compressed absorbent powder resembles a pillow(s) stuffed with the absorbent powder.

Hence, an improved fluid absorbing sheet being as thin as an ordinary bed sheet, having an even surface and being comfortable to rest on for the patient while having the capability to absorb large amounts of body fluids and/or wastes would be advantageous.

OBJECT OF THE INVENTION

One object of the present invention is to provide a fluid absorbing sheet which is thin and elastic and looks like an ordinary sheet thus taking a minimum of room when folded. Consequently, this sheet will not take a lot of storing place (before use) or waste place (after use).

An additional object of the present invention is to reduce the consumption of fluid absorbing sheets, mats or pads in maternity or delivery rooms and/or operating or surgery rooms and/or ambulance cars and/or other possible areas of application.

A further object of the invention is to reduce the time, resources and manpower used for tidying-up and/or cleaning-up of maternity or delivery rooms and/or operating or surgery rooms and/or ambulance cars.

A further object of the present invention is to provide a fluid absorbing sheet for collection of body fluids and/or other body wastes, such as for example blood, amniotic fluids, placenta, urine, organs or parts of organs, etc. During certain occurrences connected to medically related areas, emergency situations and health care, such as for example during delivery or surgery, especially large amount of body fluids and/or other body wastes will appear, sometimes abruptly. Accordingly, it is a further object of the invention to provide a fluid absorbing sheet capable of handling also the bulk of body fluids and/or wastes.

A further object of the present invention is to provide a fluid absorbing sheet capable of collecting body fluids and/or other body wastes in a controlled way such that the sheet can be an aid to determine the loss of body fluids and/or other body wastes, e.g., the loss of blood.

One further object of the invention is to provide a fluid absorbing sheet which can cover the entire surface of the base where the patient is placed in order to protect for example the (entire) mattress, bed and bed equipment or stretcher.

Yet another object of the invention is to provide methods of manufacturing such sheets, as well as their use.

It is a further object of the present invention to provide an alternative to the prior art.

It may also be seen as an object of the present invention to provide fluid absorbing sheets and methods for producing such sheets solving the above-mentioned problems of the prior art.

SUMMARY OF THE INVENTION

Thus, the above described objects and several other objects are intended to be obtained in a first aspect of the invention by providing a fluid absorbing sheet and a method for producing such a sheet according to the claims.

The present invention provides a fluid absorbing sheet which is as thin as an ordinary bed sheet. More precisely the fluid absorbing sheet comprising an upper layer of diffusing material, a middle layer of super absorbent polymer (SAP) for absorbing of body fluids and a bottom- or under-layer of water- or fluid-tight material is less than 0.70 mm thick before use and preferably the thickness is in the range of 0.40-0.65 mm and most preferred in the range of 0.50-0.60 mm. This fluid absorbing sheet can cover and protect the (entire) mattress, stretcher, bed or bed equipment from wear and tear and/or getting wet.

One aspect the present invention is to provide a fluid absorbing sheet comprising a bottom- or under-layer of water- or fluid-tight material, a middle layer of super absorbent polymer (SAP) and an upper layer of diffusing material, wherein said super absorbent polymer (SAP) is in powder form and is attached onto the under-layer, and said upper layer covers the middle layer of super absorbent polymer (SAP) and is attached to the under-layer at least in the edge areas. The fluid absorbing sheet further comprises at least one water- or fluid-tight bag for collecting and/or disposing of body fluids and/or other body wastes.

Another aspect of the invention is to provide a fluid absorbing sheet comprising one or several, e.g. two, three or more, additional absorbing layers comprising an upper layer of diffusing material, a middle layer of super absorbent polymer (SAP) and a bottom- or under-layer of water- or fluid-tight material, provided and attached onto the sheet according to the present invention at least in the area where the excess or bulk of body fluids is expected, wherein said at least one additional layer is fastened to the sheet according to the present invention in such a way that it/they easily can be torn or removed after absorbing a certain amount of fluids, e.g. body fluids.

A further aspect of the invention is to provide a method of manufacturing fluid absorbing sheets according to the present invention, comprising the following steps: applying or attaching a layer of pulverized super absorbent polymer (SAP) onto a water-tight bottom-layer of the sheet according to the invention; if necessary, the excess of super absorbent polymer (SAP) powder not attached to the bottom- or under-layer is removed; the surface of the absorbent layer is then covered with a layer of diffusing material, wherein at least the edge areas of the sheet of the present invention are suitably treated or prepared in order to fasten the layer of diffusing material to the under-layer covered with the absorbent layer; then the water- or fluid-tight bag for collecting and/or disposing of body fluids and/or other body wastes is shaped by forming an envelope or pocket by folding at the desired place of the sheet according to the invention or alternatively a ready-made water- or fluid-tight bag is attached.

The individual aspects of the present invention may each be combined with any of the other aspects. These and other aspects of the invention will be apparent from the following description with reference to the described embodiments and the enclosed drawings.

BRIEF DESCRIPTION OF THE DRAWINGS

The fluid absorbing sheets and the method for producing the sheet according to the invention will now be described in more detail with regard to the accompanying drawings. The drawings show one way of implementing the present invention and are not to be construed as being limiting to other possible embodiments falling within the scope of the attached claim set.

FIG. 9a-9c show one embodiment of the fluid absorbing sheet according to the invention where the water-tight bag is an integrated part of the sheet, and the steps for folding the bag, FIG. 10a-c show another embodiment of the fluid absorbing sheet according to the invention where the water-tight bag is an integrated part of the sheet, and the steps for folding the bag.

DETAILED DESCRIPTION OF THE EMBODIMENTS

Figure 1:
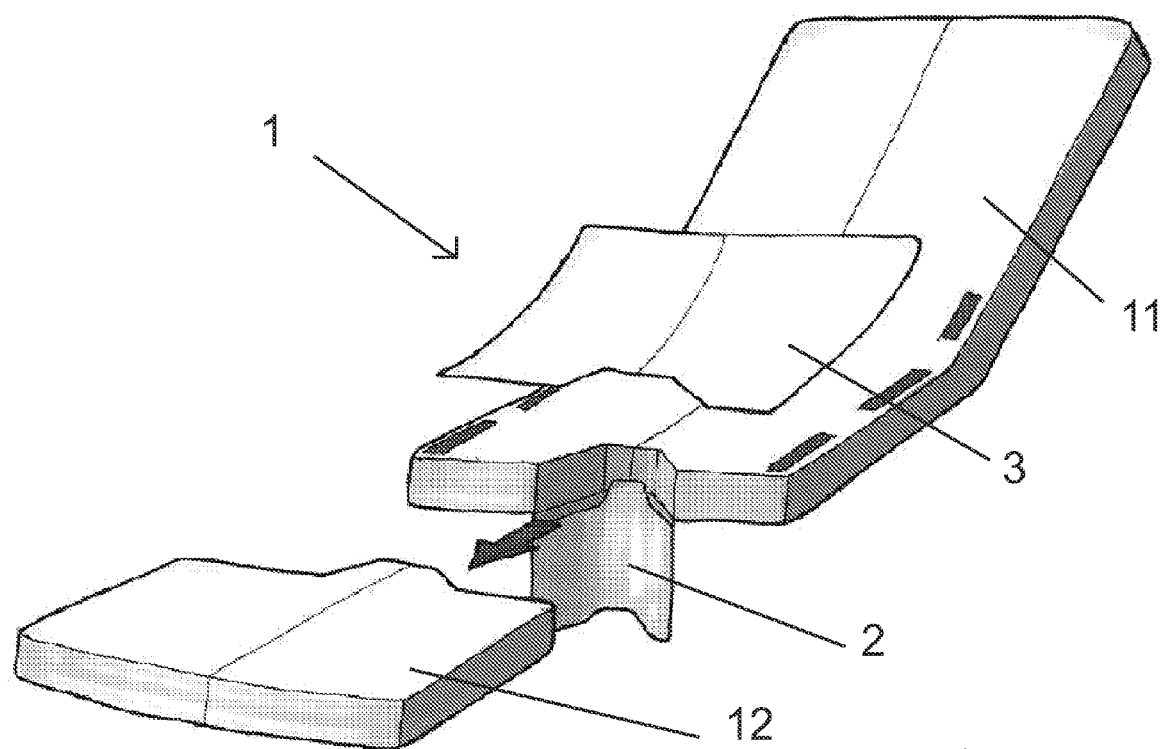
FIG. 1 shows a fluid absorbing sheet according to the present invention.

FIG. 1 illustrates a fluid absorbing sheet 1 according to the present invention. Modern maternity or delivery beds usually consist of two parts, e.g. Affinity® III or IV from Hill-Rom. Therefore, a set of sheets 11, 12 being fit or adapted to the shape of the bed is needed. The sheet 1 according to the present invention can be designed to fulfil these needs, and the final product can also be sold as a set 1 of fluid absorbing sheets 11, 12. However, the fluid absorbing sheet according to the present invention can be designed and/or shaped for use not only in maternity or delivery rooms, but also in operating or surgery rooms and/or ambulance cars, etc. The fluid absorbing sheet 1 according to the invention comprises a bottom- or under-layer of water- or fluid-tight material, a middle layer of super absorbent polymer (SAP) and an upper layer of diffusing material, as well as at least one water- or fluid-tight bag 2. The bottom layer is intended to protect the (entire) mattress, stretcher, bed and bed equipment from wear and tear and/or getting wet. The middle layer serves to absorb fluids, and particularly body fluids such as for example blood, amniotic fluids, urine, etc. The upper layer is used to cover the absorbent and has the ability to diffuse or permeate the fluids there through. The upper layer also gives the user a feeling of dryness and comfort. The purpose of the at least one water- or fluid-tight bag 2 is for collecting and/or disposing of the bulk body fluids and/or other body wastes.

The upper layer of diffusing material should have a hydrophilic surface to ensure fast absorption of fluid. As a diffusing material layer a non-woven textile can be used. Non-woven fabrics are broadly defined as sheet or web structures bonded together by entangling fibres or filaments (and by perforating films) mechanically, thermally or chemically. Other suitable diffusing materials can also be used.

The water- or fluid-tight material of the bottom- or under-layer can be, but is not limited to, a plastic, e.g. a biodegradable bioplastic (e.g. the bioplastic sold under the trademark BIOBAG®). The sheet 1 can be designed and intended to have as few parts and/or seams as possible in order to avoid punctures/stitches and/or connections/joints in the plastic material.

Super absorbent polymers are polymers that can absorb and retain extremely large amounts of liquid relative to their own mass. Accordingly, different types of such polymers have been widely used in personal hygiene products, baby diapers, adult protective underwear and sanitary napkins. The material known as NORSOCRYL® S35 can be used for the middle layer of super absorbent polymer (SAP). NORSOCRYL® S35 is the trade name for copolymers based on sodium acrylate. The super absorbent polymer (SAP) is in powder form. The particle size of the powder is important with respect to the comfort of the patient resting on the sheet as well as the absorption properties and can be in the range of 10-75 μm, preferably 15-50 μm. Other suitable super absorbent polymers based on polyacryl acid and in powder form can also be used. Further examples of useable super absorbent polymers are, e.g., Sephacryl®, polydextran (Sephadex®), polysacharid, and the like.

The pulverized super absorbent polymer (SAP) can be glued directly onto the fluid-tight under-layer by an adhesive or glue, e.g. contact glue. The absorbent powder which has not glued properly, i.e. which is not affixed, onto the under-layer can be removed by means of appropriate methods such as, e.g., gravity, blowing, suction, vacuum, hovering, etc. The amount of super absorbent powder attached to the under-layer can be as high as 60-70 $g/m^2$ with a thickness of the absorbing layer of about 0.05-0.10 mm. However, it is preferred to apply less super absorbent to avoid local swelling. Preferably the amount of super absorbent polymer should be from 50-5 $g/m^2$, 45-10 $g/m^2$, 40-15 $g/m^2$, 35-20 $g/m^2$, 30-25 $g/m^2$, 30-20 $g/m^2$ or 25-10 $g/m^2$, most preferred about 30 $g/m^2$. Then the surface covered with the absorbent will be covered with the diffusing upper layer and glued at least in the edge areas. The absorbing layer comprising the under-layer, middle layer and upper layer, having a thickness of less than 0.70 mm, will within seconds swell and absorb up to about 10 $l/m^2$ when the amount of absorbent is about 60-70 $g/m^2$. The maximum water absorbing or swelling capacity of this absorbing layer is about 24 $l/m^2$. In one experiment 2 liters of water was poured over 50 cm×50 cm of the absorbing layer of the invention containing 60 $g/m^2$ super absorbing polymer (NORSOCRYL® S35). The complete volume of water was absorbed in less than 10 seconds (i.e., at the speed of pouring).

The sheet 1 can have an elastic string or ribbon (not shown) attached, e.g. sewed, glued or laminated, along the sheet 1 edges (preferably on the back side) in order to get the sheet 1 to fit well and tight on the mattress. The head end of the sheet 1, particularly the back side can be suitably formed, like e.g. a "pocket" or "envelope", in order to be pulled onto the head end of the mattress, thus avoiding sliding down of the sheet 1 during use.

Different appropriate methods of attaching the powder of super absorbent polymer (SAP) onto the bottom- or under-layer can be used, e.g. chemical bonding, hydrolytic binding, heating or warming up of the plastic under-layer in order to get the powder of super absorbent polymer (SAP) fastened thereto, using a suitable thin bearer with the powder of super absorbent polymer (SAP) integrated or incorporated therein, etc.

The fluid absorbing sheet 1 according to the invention comprises at least one water- or fluid-tight bag 2 for collecting and/or disposing of body fluids and/or other body wastes. The bag 2 can constitute an integrated part of the sheet 1, i.e. being formed by folding a part of the sheet 1 it self to an envelope or pocket at the desired place of the sheet 1 where the excess or bulk of body fluids and/or wastes is expected, or the bag 2 can be a ready-made bag attached in the proximity of or to an area of the sheet 1 where the excess or bulk of body fluids and/or wastes is expected.

In order to keep the body fluids in the attached bag and to avoid spill, the inside of the bag can be partly or completely covered with super absorbent polymer (SAP).

The fluid absorbing sheet 1 according to the invention can further comprise at least one additional absorbing layer 3 comprising an upper layer of diffusing material, a middle layer of super absorbent polymer (SAP) and a bottom- or under-layer of water- or fluid-tight material, being provided and attached onto the sheet 1 at least in the area where the excess or bulk of body fluids is expected, wherein said at least one additional layer 3 is fastened to the sheet 1 in such a way that it/they can easily be torn or removed after absorbing a certain amount of fluids, e.g. body fluids.

The fluid absorbing sheet 1 according to the invention can be an aid to determine the loss of body fluids and/or other body wastes, e.g., the loss of blood during surgery. By way of example only the bag or the complete sheet can be removed and weighed, and the loss of e.g. blood can be calculated by subtracting the specific weight of the bag or the complete sheet, respectively.

Figure 2A:
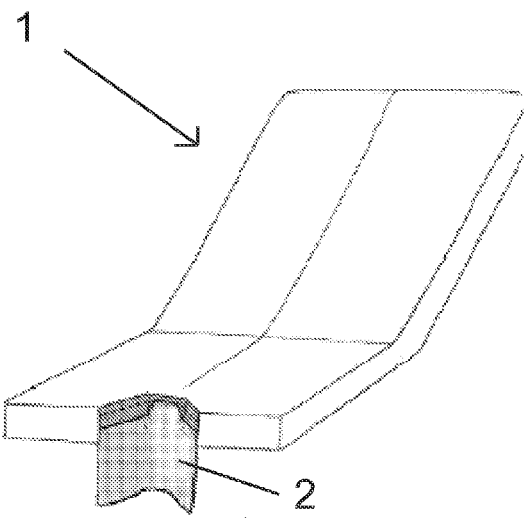
FIG. 2a-2b illustrate different embodiments of the fluid absorbing sheet according to the present invention where the water-tight bag has different positions.
Figure 2B:
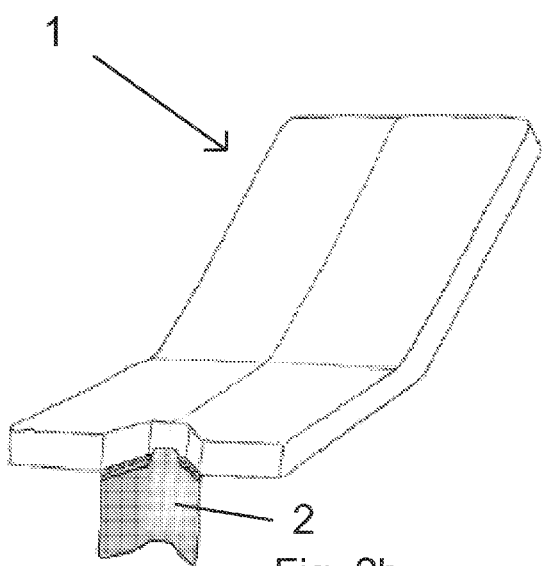

FIGS. 2a and 2b show different positions for placing of the bag 2 onto the fluid absorbing sheet 1 according to one embodiment of the invention, wherein the sheet 1 is designed for a modern maternity or delivery bed comprising two parts. On FIG. 2a the water-tight bag 2 is placed or attached to the sheet in such a way that it will appear on the top edge of the mattress, while on FIG. 2b the water-tight bag 2 is placed or attached to the sheet in such a way that it will appear on the lower edge of the mattress.

Figure 3A:
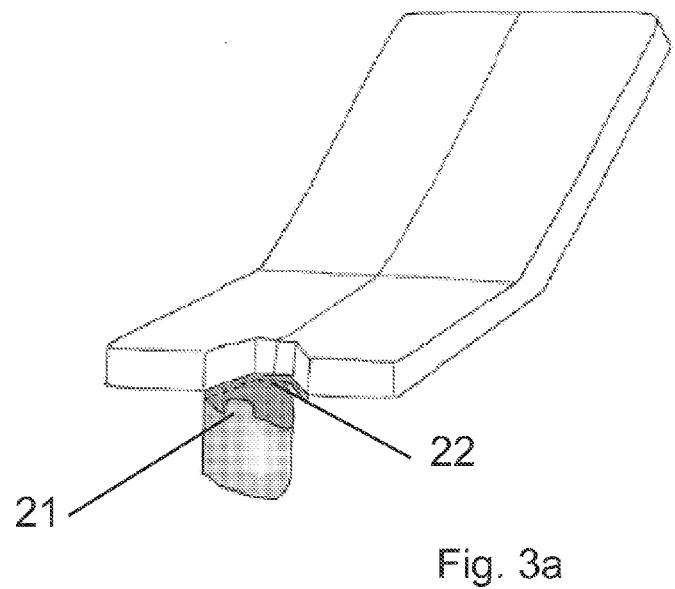
FIG. 3a-3c show different embodiments of the fluid absorbing sheet according to the present invention with different examples for removing and/or sealing of the water-tight bag.
Figure 3B:
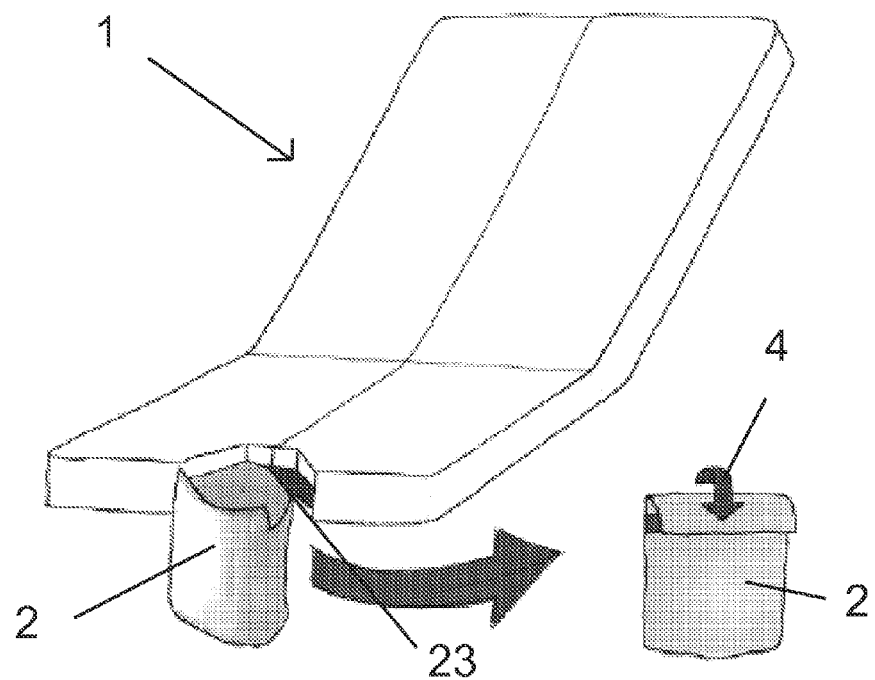
Figure 3C:
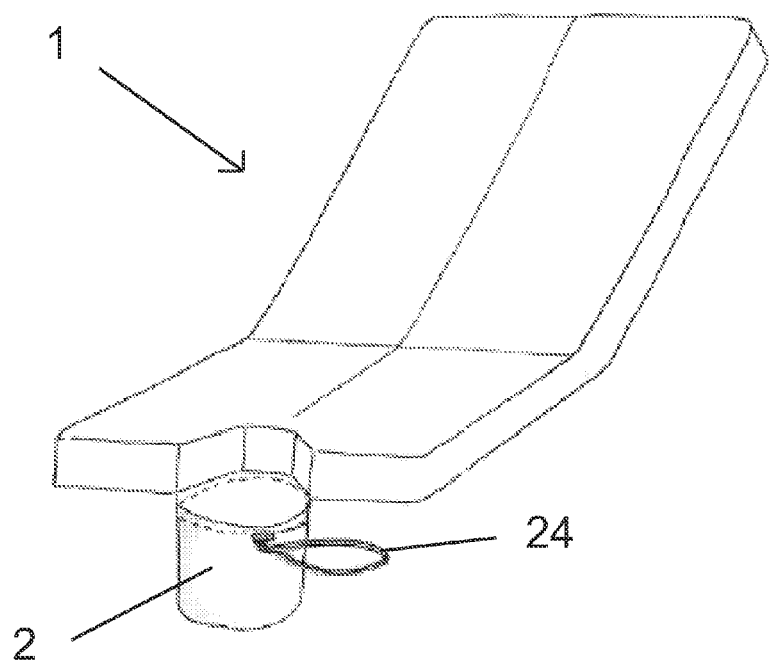

FIG. 3a-3c show different embodiments of the fluid absorbing sheet 1 according to the present invention with different examples for removing and/or sealing of the water-tight bag 2. On FIG. 3a the bag 2 edge can for example be sewed, glued or laminated to the sheet 1. Additionally the bag 2 can have perforations 22 in order to ease the tearing of the bag 2 and its removing from the sheet 1. The bag 2 can also have means 21 for easy pulling out and opening of the bag 2 in order to receive thereafter the body fluids and/or wastes therein. On FIG. 3b the bag 2 is attached to the sheet 1 by means of Velcro® or tape 23. The same Velcro® or tape 23 means and/or additional tape or Velcro® can be used to lock 4 and/or seal the bag 2. On FIG. 3c it is shown that a string or cord 24 can be used in order to close the bag 2.

Figure 4:
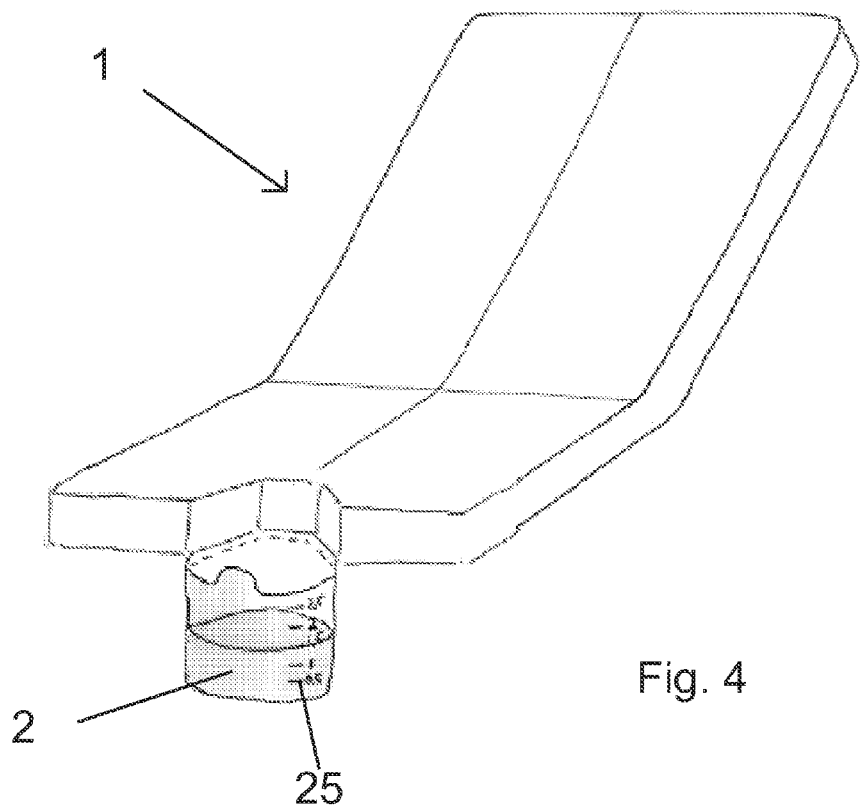
FIG. 4 shows one embodiment of the fluid absorbing sheet according to the invention, wherein the water-tight bag is transparent or semitransparent and with a divided scale.

At least one part or the whole of the water-tight bag 2 can be transparent or semitransparent, as shown in FIG. 4. The bag 2 can in addition have a divided scale 25 allowing the body fluids and/or wastes collected therein to be measured, e.g. weight (in kilos or grams), volume (in liters, deciliters (dl) or $cm^3$), etc.

Figure 5A:
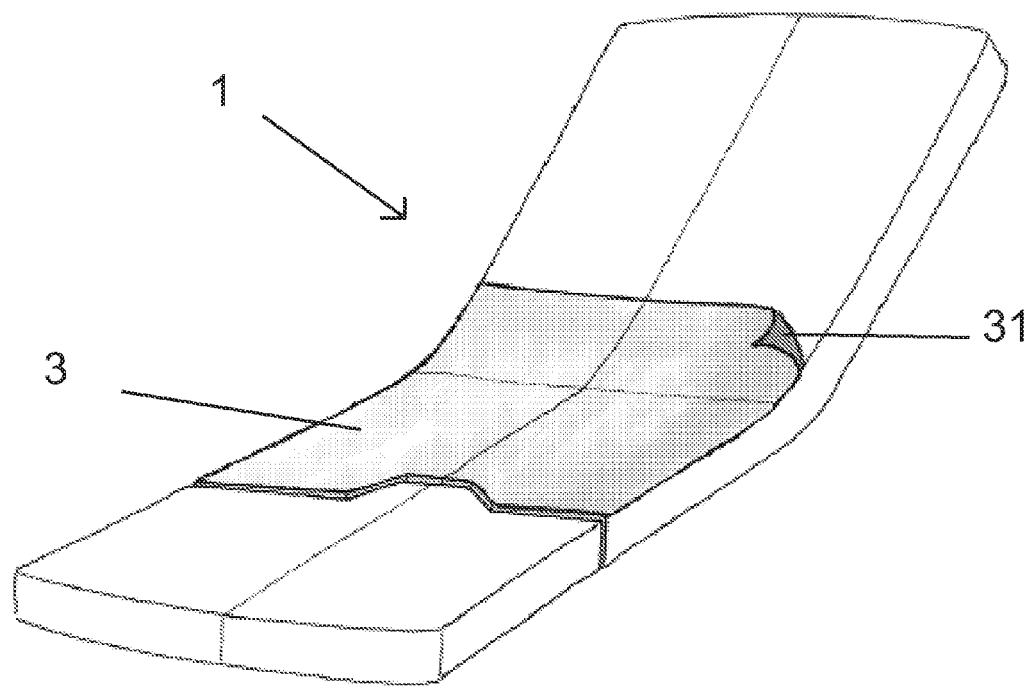
FIG. 5a-5b illustrate different embodiments of the fluid absorbing sheet according to the invention comprising an additional absorbing layer(s) attached to the sheet in different ways.
Figure 5B:
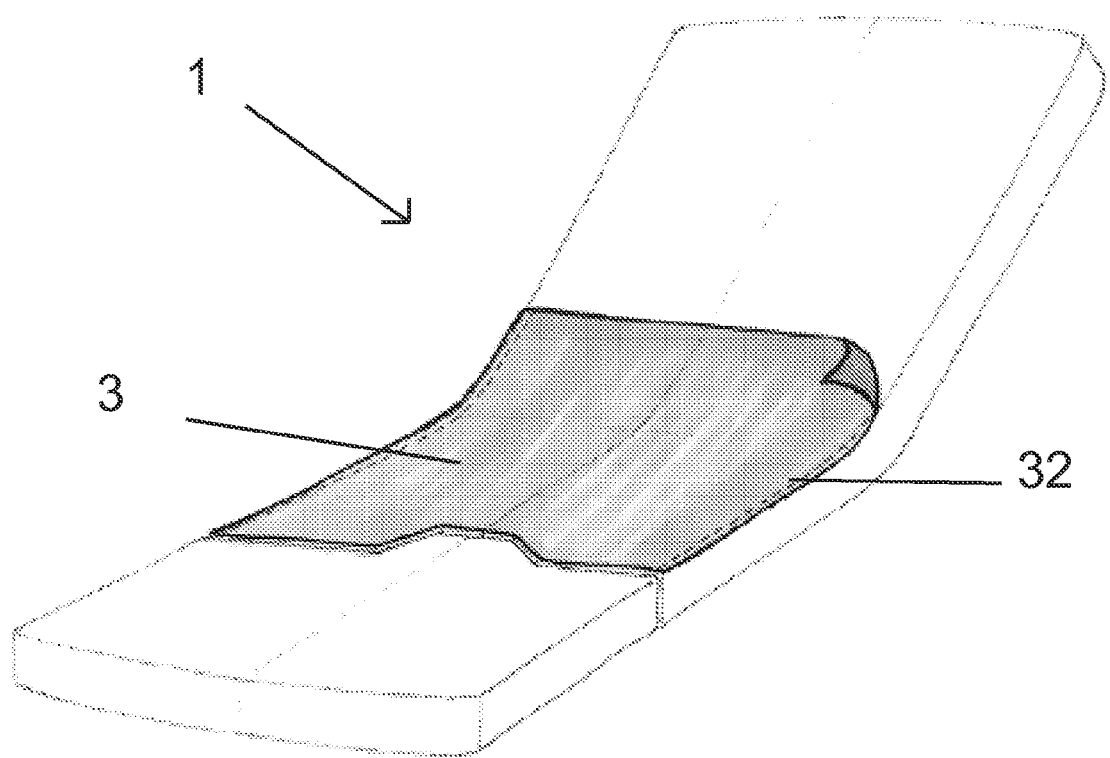

FIG. 5a-5b illustrate different embodiments of the fluid absorbing sheet 1 according to the invention, wherein said at least one additional layer 3 of absorbing sheet is attached to the sheet 1 in different exemplification ways. On FIG. 5a said at least one additional layer 3 can have on its entire backside a suitable adhesive or glue, tape, or Velcro® 31 so that the additional layer 3 will easily be removed or torn from the sheet 1. On FIG. 5b said at least one additional layer 3 can be sewed or glued or laminated to the sheet 1 at least in its edge areas. Additionally said layer 3 can have perforations 32 (e.g.

along the long sides of the mattress/sheet) for easing the removing or tearing of the top layer of said additional layers 3 from the sheet 1.

Figure 6A:
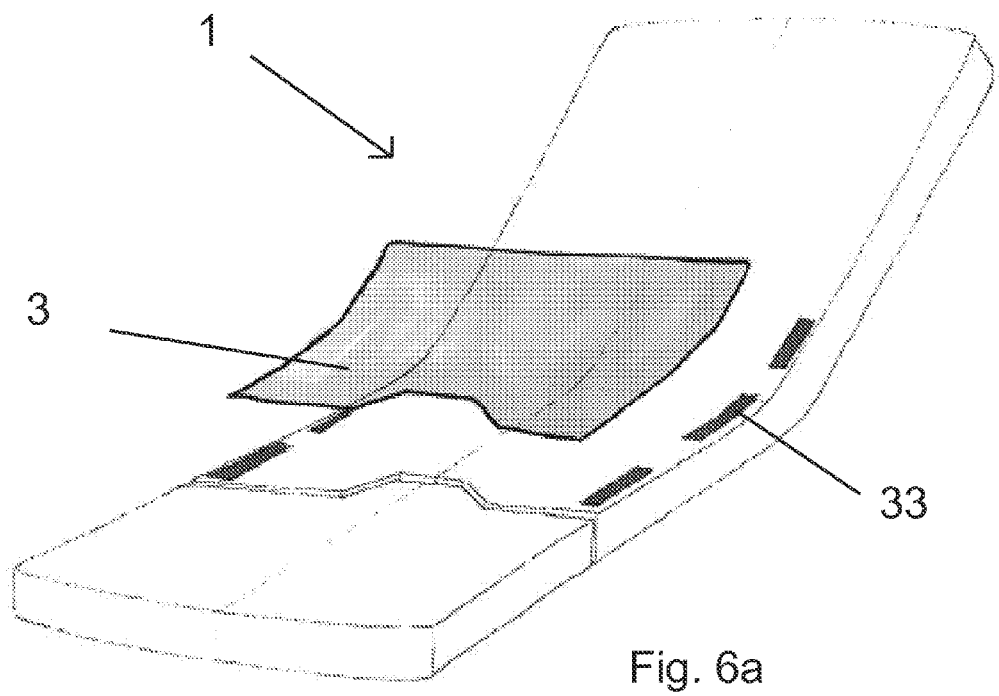
FIG. 6a-6c show further embodiments of the fluid absorbing sheet according to the invention comprising an additional absorbing layer(s) attached to the sheet by means of tape or Velcro®.
Figure 6B:
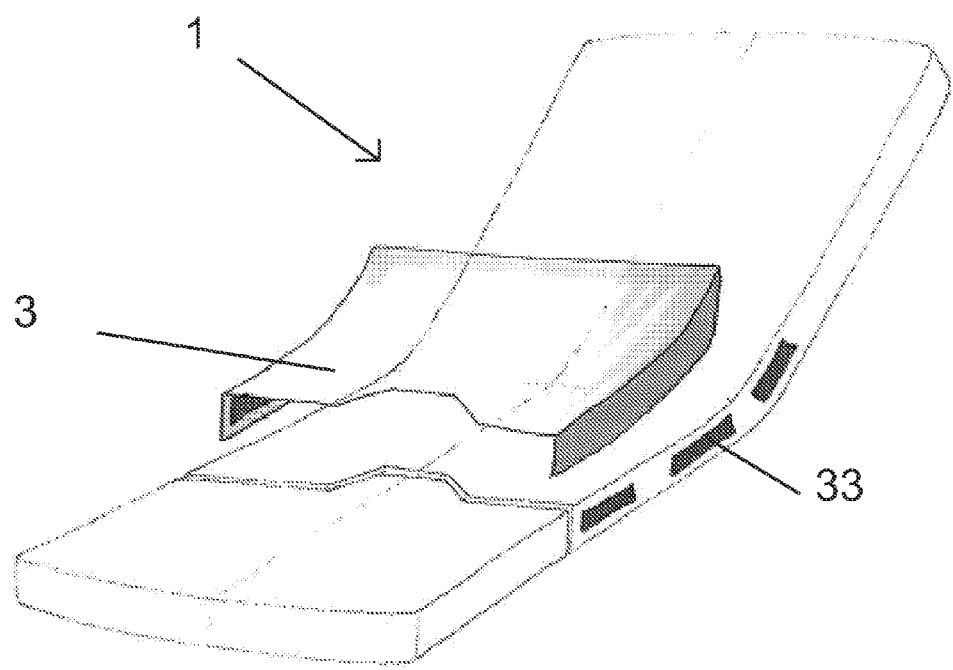
Figure 6C:
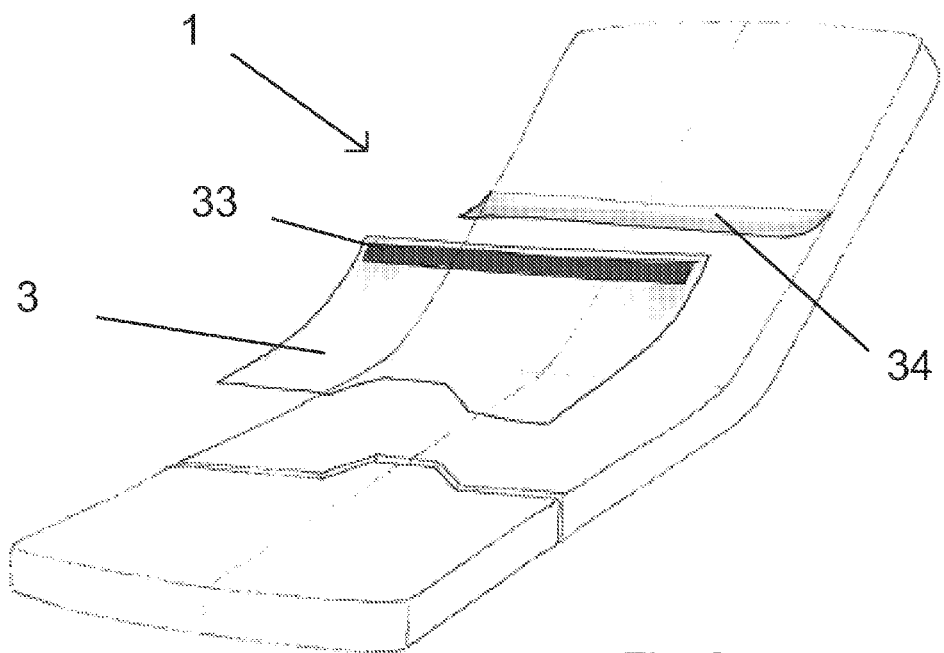

FIG. 6a-6c show further embodiments of the fluid absorbing sheet 1 according to the invention, wherein said at least one additional layer 3 of absorbing sheet is attached to the sheet 1 in different exemplification ways by means of tape or Velcro® 33. On FIG. 6a said tape or Velcro® attaching means 33 is arranged to be placed on top of the mattress and along its two long side or edge areas. On FIG. 6b said tape or Velcro® attaching means 33 is arranged to be placed along the two long vertical sides of the mattress. On FIG. 6c said tape or Velcro® attaching means 33 of the additional layer is arranged to be attached to or removed from a flap 34 having tape or Velcro® respectively and being attached to the sheet 1.

Figure 7A:
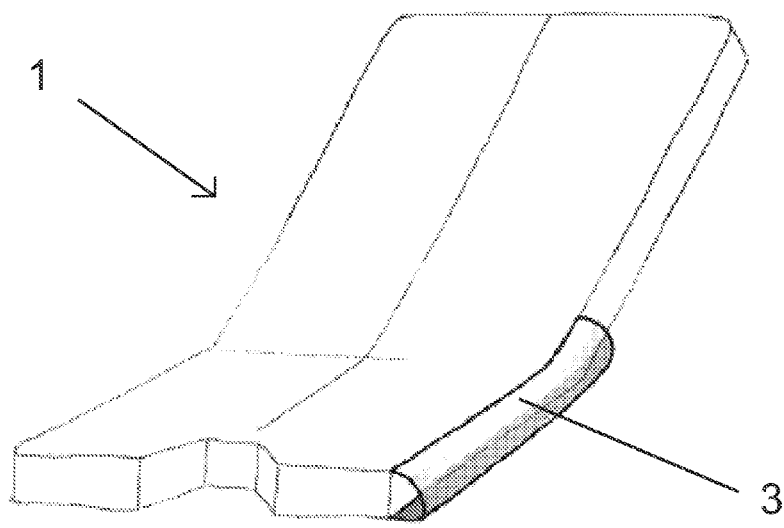
FIG. 7a-7b show an additional embodiment of the fluid absorbing sheet according to the invention comprising at least one additional layer of absorbing sheet suitably attached to one of the two long sides of the sheet/mattress.
Figure 7B:
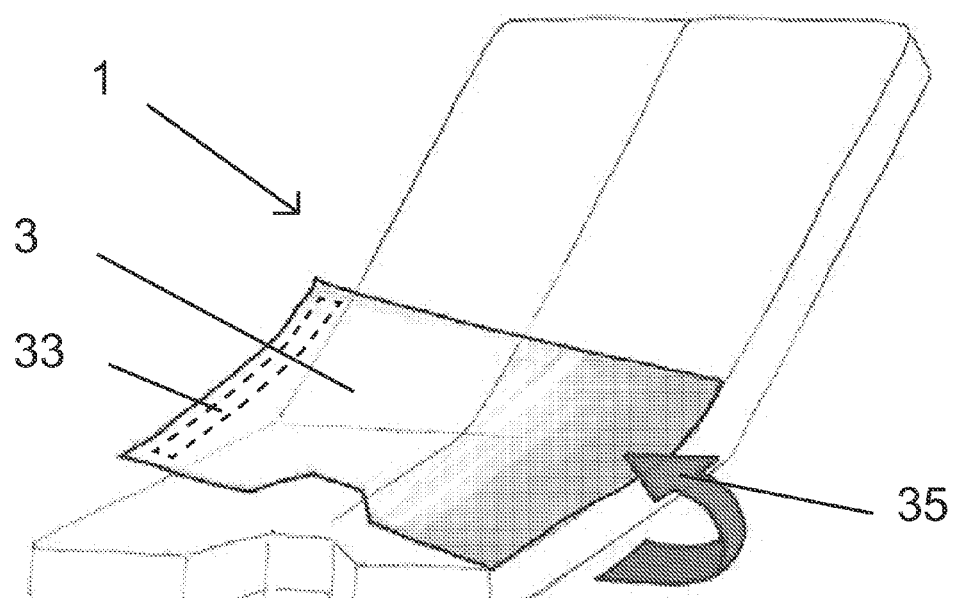

FIG. 7a-7b show an additional embodiment of the fluid absorbing sheet 1 according to the invention, wherein said at least one additional layer 3 of absorbing sheet is suitably attached, e.g. by gluing, sewing, laminating, etc., to one of the long sides of the sheet 1/mattress and can be put under the mattress or rolled/folded along the long vertical side of the mattress or can just be hanging down (FIG. 7a). The attached side of said at least one additional layer 3 can additionally have perforations for easy removing from the main sheet 1. When necessary said additional layers 3 can one by one or all together be pulled or drawn out and set over 35 the area of the main sheet 1 where the excess or bulk of body fluids is expected (FIG. 7b). At the other long side of the sheet 1/mattress said at least one additional layer 3 can have suitable attaching means 33, such as for example tape or Velcro®, in order to get said at least one additional layer 3 attached to the main sheet 1 at least on both long sides.

Figure 8A:
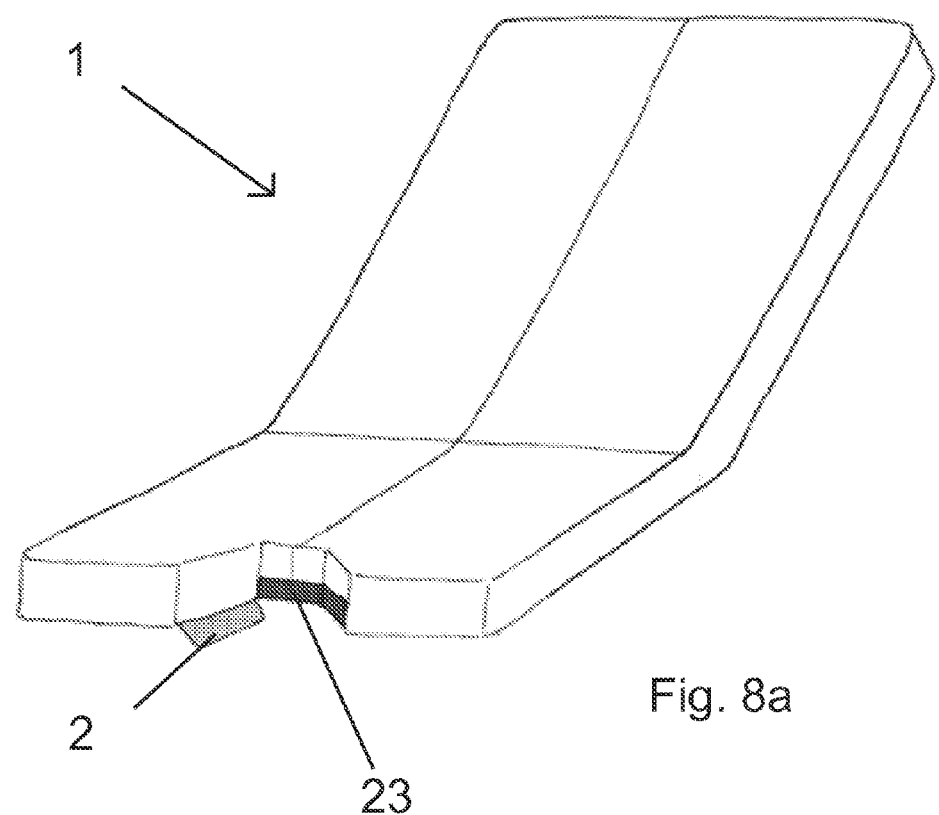
FIG. 8a-8e show different embodiments and placements of said at least one water- or fluid-tight bag of the sheet according to the invention.
Figure 8B:
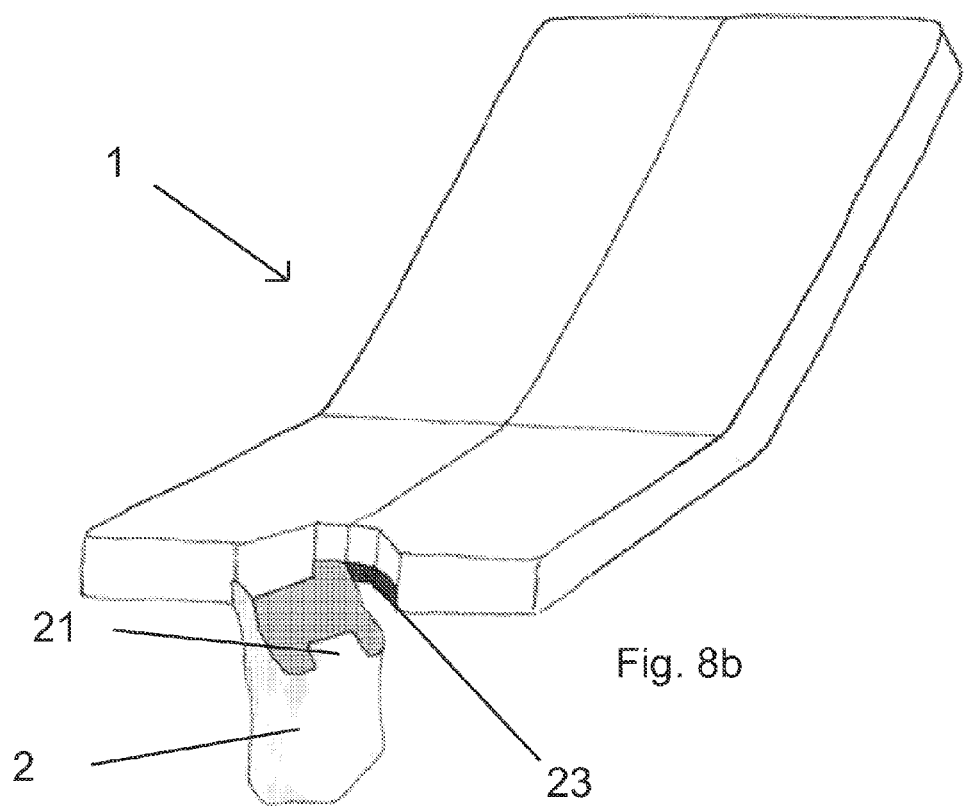
Figure 8C:
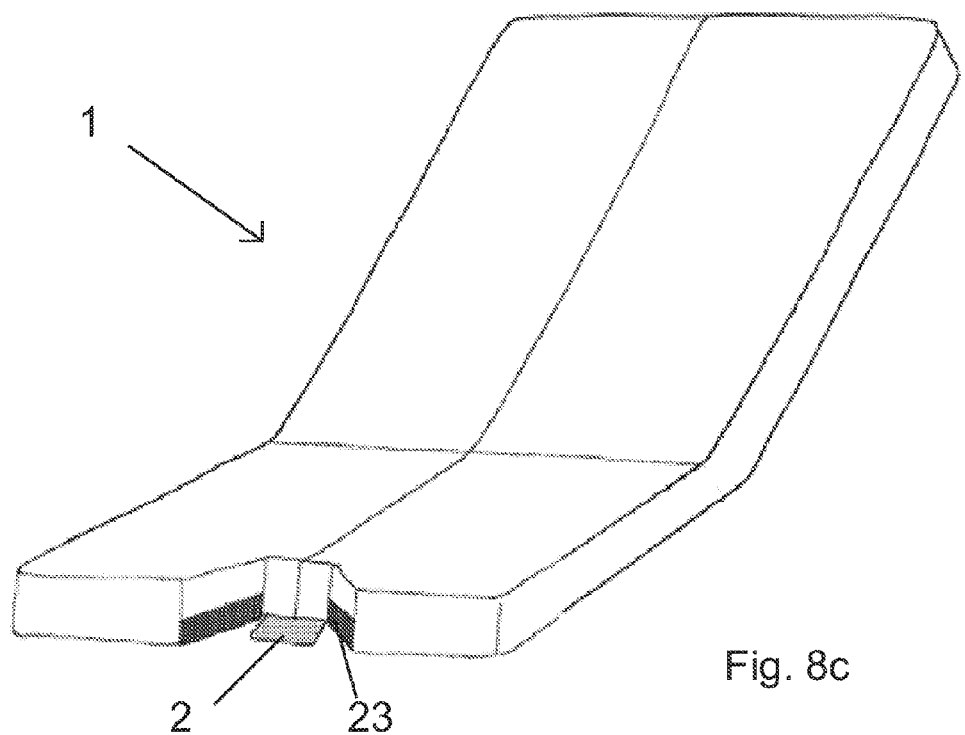
Figure 8D:
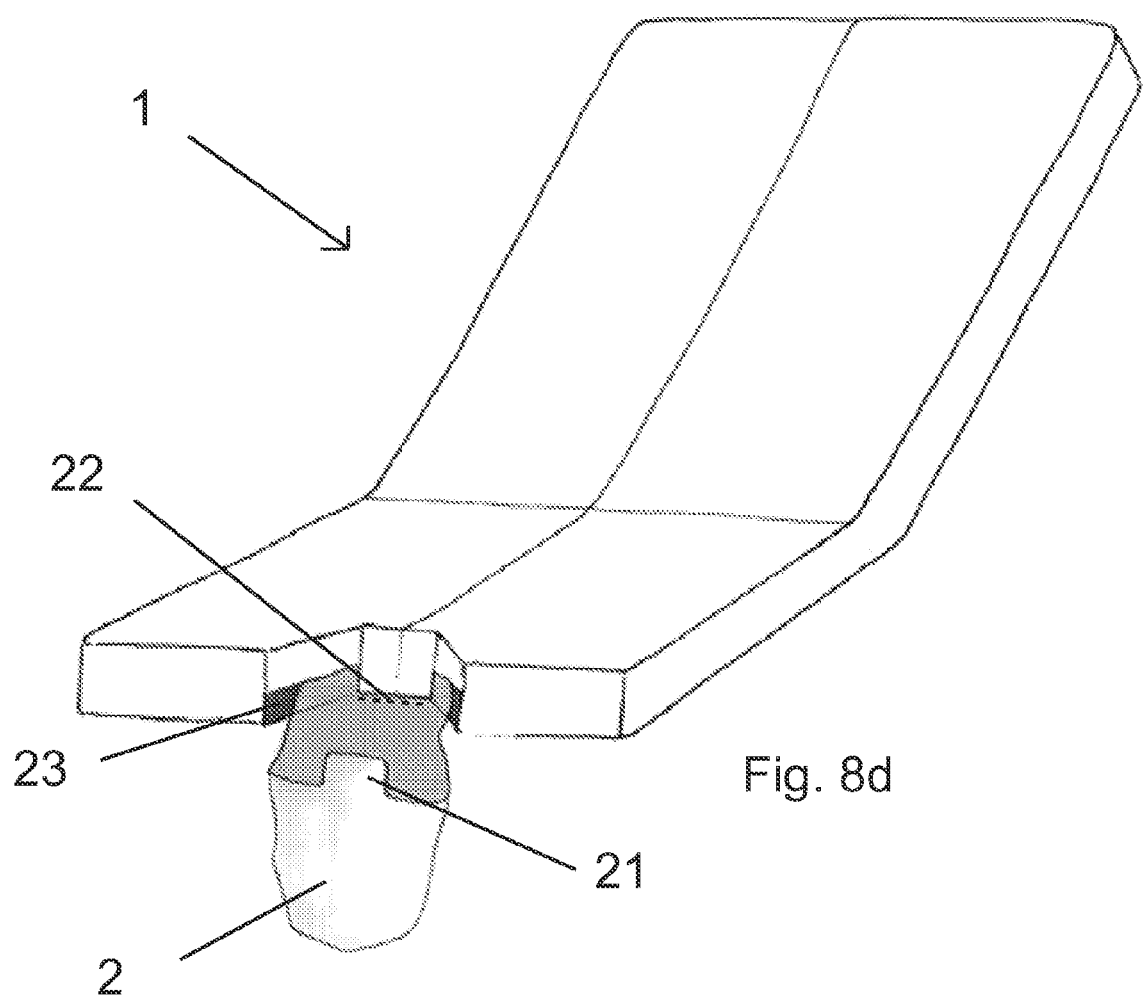
Figure 8E:
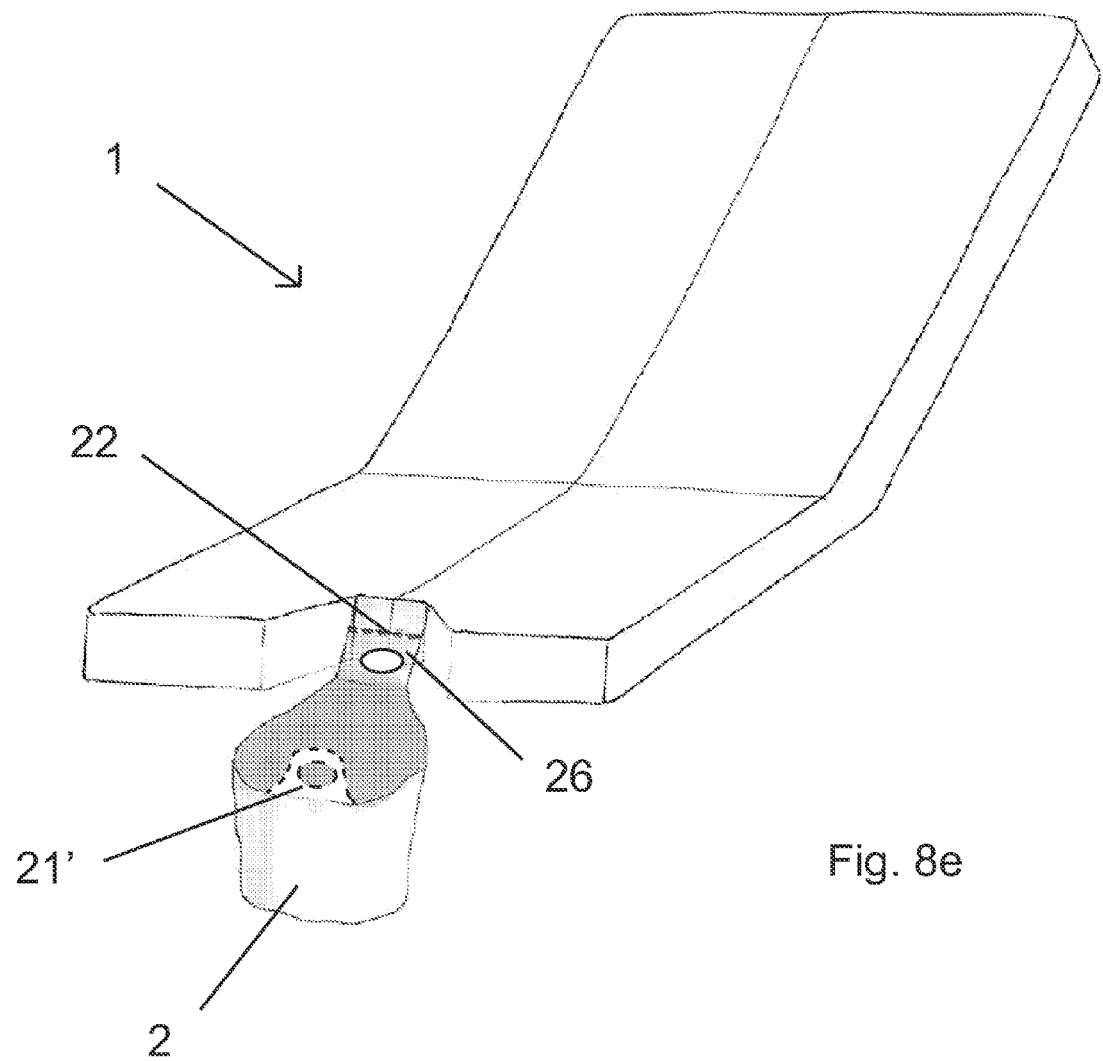

FIG. 8a-8e illustrate different embodiments and placement arrangements of said at least one water- or fluid-tight bag 2 of the sheet 1 according to the invention. Before use the bag 2 can be folded or rolled or put/stacked under the mattress (FIGS. 8a and 8c). Additionally, in order to ease and/or simplify the pulling out and opening of the bag 2, the bag 2 can comprise suitable pulling-out and opening means 21, e.g. projecting edge or shoulder or ear or arm or string/cord or ribbon (FIGS. 8b and 8d). A combination of different attachment means and/or methods can be used in order to attach the bag 2 to the sheet 1. For example part of the bag 2 edge can be sewed or glued or laminated to the sheet 1, alternatively it might additionally have some perforations 22 (FIGS. 8d and 8e), and the rest of the bag 2 edge can be further attached 23, e.g. by means of tape or Velcro®, to the sheet 1 (FIG. 8a-8d). Furthermore, the bag 2 can be attached to the sheet 1 in such a way that it will be hold, partially or completely, open and ready for receiving the body fluids and/or wastes (e.g. FIGS. 8b and 8d). The bag 2 can comprise at least one handle 26 (FIG. 8e). Additionally and/or alternatively said means 21 for easy pulling out and opening of the bag 2 can have a hole in order to also be used as a handle 21' (FIG. 8e).

FIGS. 9a-9b illustrate an embodiment of the invention where the bag 2 constitutes an integrated part of the sheet 1, i.e. the bag 2 is made by folding the sheet it self into a bag. The different steps of folding are shown in FIG. 9a-9c, starting in FIG. 9a. In FIG. 9a the folding lines are indicates as dotted lines on the upper layer of the sheet 1 facing up (striped). In FIG. 9b the sheet 1 is folded as indicated by the dotted lines simultaneously as the two corners of the sheet are lifted towards the outer point of the folding lines (indicated by arrows on each side). As can be seen the end of the sheet starts to form a light arch. The folding continues into FIG. 9c showing the formed bag 2 where the black colour indicates the back side of the sheet/under-layer. The diagonal stripes of the flaps illustrate the upper layer of the sheet which has been folded but still is facing up. The arch is more pronounced indicating the outer edge of the formed bag. The back of the flaps can then be glued to the back of the sheet/under-layer to permanently form the bag. The bag 2 has a pocket-like shape.

FIGS. 10a-10b illustrate another embodiment of the invention where the bag 2 constitutes an integrated part of the sheet 1, i.e. the bag 2 is made by folding the sheet it self into a bag. Here the bag 2 is prepared by a method different from the one shown in FIG. 9a-9c. The different steps of folding are shown in FIG. 10a-10c, starting in FIG. 10a. FIG. 10a shows two triangles 5 indicated by dotted lines on the upper layer of the sheet 1 facing up (striped). These triangles 5 are removed, e.g. by shearing or cutting. Then, in FIG. 10b, the remaining end of the sheet is starting to get folded over (indicated by arrows). The black colour indicates the back side of the sheet 1/under-layer. The folding continues until the end of the sheet 1 meets the short side of the removed triangles (FIG. 10c). The arch in FIG. 10c indicates the outer edge of the formed bag, where the black colour indicates the back side of the sheet/under-layer. The bag has an envelope-like shape. The part of the sheet 1 being broader than the bag 2 can be folded and attached under, for example, the mattress.

The bag 2 will be in the proximity of or to an area of the sheet 1 where the excess or bulk of body fluids and/or wastes is expected.

Furthermore, the invention relates to a method of manufacturing a fluid absorbing sheet 1 according to the invention, wherein the thickness of the sheet 1 is reduced by gluing pulverized super absorbent polymer (SAP) directly onto the water-tight bottom-layer of the sheet 1. The glue and the pulverized super absorbent polymer can be sprayed or showered simultaneously and/or after each other onto the water-tight bottom-layer, and then (after drying) the excess of powder not affixed to the under-layer can be removed. Then the surface with the absorbent is covered with the layer of diffusing material and at least the edge area of the sheet of the present invention is spayed with glue in order to fasten the layer of diffusing material to the water-tight bottom-layer covered with the absorbent.

The invention further relates to a method of manufacturing the thin fluid absorbing sheet 1 according to the present invention, comprising the following steps:
applying or attaching a layer of pulverized super absorbent polymer (SAP) onto a water-tight bottom-layer of the sheet 1;
if necessary, removing the excess of super absorbent polymer (SAP) powder not attached to the bottom- or under-layer; and
covering the surface of the absorbent layer with a layer of diffusing material, wherein at least the edge areas of the sheet 1 are suitably treated or prepared in order to fasten the layer of diffusing material to the water-tight bottom-layer covered with the absorbent layer;
shaping the water- or fluid-tight bag 2 for collecting and/or disposing of body fluids and/or other body wastes by forming an envelope or pocket at the desired place of the fluid absorbing sheet (1) or alternatively attaching a ready-made water- or fluid-tight bag (2).

The super absorbent polymer (SAP) can be sprayed or showered onto the water-tight bottom-layer together with and/or after an adhesive or glue or glue agent. Adhesive or glue is a compound in a liquid or semi-liquid state that adheres or binds items together. The glue is preferably a contact glue.

In an alternative embodiment of the invention the super absorbent polymer (SAP) can be laminated to the water-tight under-layer.

In yet another embodiment of the invention the super absorbent polymer (SAP) can be chemically bound to the bottom- or under-layer.

Furthermore, the fastening of the diffusing material layer to the absorbent layer applied upon the water-tight bottom-layer can be done by laminating the diffusing material layer onto the water-tight bottom-layer at least in the edge areas of the sheet 1. Alternatively, at least the edge areas of the sheet 1, i.e. the upper layer, the under-layer or both, can be spayed with glue in order to fasten the layer of diffusing material to the water-tight bottom-layer covered with absorbent.

According to one embodiment of the invention at least one water- or fluid-tight bag 2 for collecting and/or disposing of body fluids and/or other body wastes can be attached or fastened in the proximity of or to an area of the sheet 1 where the excess or bulk of body fluids and/or wastes is expected.

It is also possible to have at least one additional absorbing layer 3 comprising an upper layer of diffusing material, a middle layer of super absorbent polymer (SAP) and a bottom- or under-layer of water- or fluid-tight material, attached or fastened onto the sheet 1 at least in the area where the excess or bulk of body fluids is expected, and in such a way that the most upper layer 3 thereof easily can be torn or removed from the sheet 1 after absorbing a certain amount of fluids, e.g. body fluids. In this way the fluid absorbing sheet 1 can be used longer while the comfort of the patient is kept since it is possible to remove and discard only the additional absorbing layer. This will accordingly reduce the consumption of fluid absorbing sheets.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A fluid absorbing sheet comprising:
   a bottom- or under-layer of water- or fluid-tight material;
   a middle layer of super absorbent polymer (SAP); and
   an upper layer of diffusing material,
   wherein said super absorbent polymer (SAP) is in a powder form, the powder having a particle size between 10-75 um, and is attached onto the under-layer, and said upper layer covers the middle layer of super absorbent polymer (SAP) and is attached to the under-layer at least in the edge areas,
   wherein said fluid absorbing sheet further comprises at least one water- or fluid-tight bag for collecting or disposing of body fluids or other body wastes and,
   wherein the thickness of said fluid absorbing sheet is less than 0.70 mm, and further wherein the bottom- or under-layer of the water- or fluid-tight material is a biodegradable bioplastic.

2. The fluid absorbing sheet according to claim 1, wherein said super absorbent polymer (SAP) is attached onto the under-layer by glue or adhesive.

3. The fluid absorbing sheet according to claim 1, wherein the super absorbent polymer (SAP) is a copolymer comprising sodium acrylate, and the diffusing material of the upper layer is a non-woven textile.

4. The fluid absorbing sheet according to claim 1, wherein the at least one water- or fluid-tight bag for collecting or disposing of body fluids or other body wastes constitutes an integrated part of the sheet placed where the excess or bulk of body fluids or wastes is expected.

5. The fluid absorbing sheet according to claim 1, wherein the at least one water- or fluid-tight bag for collecting or disposing of body fluids or other body wastes is attached in the proximity of or to an area of the sheet where the excess or bulk of body fluids or wastes is expected.

6. The fluid absorbing sheet according to claim 5, wherein the inside of the at least one water- or fluid-tight bag is partly or completely covered with super absorbent polymer (SAP).

7. A method of manufacturing a fluid absorbing bed sheet, the fluid absorbing sheet comprising:
   a bottom- or under-layer of water- or fluid-tight material;
   a middle layer of super absorbent polymer (SAP); and
   an upper layer of diffusing material,
   wherein said super absorbent polymer (SAP) is in a powder form and is attached onto the under-layer, and said upper layer covers the middle layer of super absorbent polymer (SAP) and is attached to the under-layer at least in the edge areas,
   wherein said fluid absorbing sheet further comprises at least one water- or fluid-tight bag for collecting or disposing of body fluids or other body wastes and,
   wherein the thickness of said fluid absorbing sheet is less than 0.70 mm, and further wherein the bottom- or under-layer of the water- or fluid-tight material is a biodegradable bioplastic, the method of manufacturing the fluid absorbing bed sheet comprising:
   applying or attaching a layer of super absorbent polymer (SAP) in powder form onto a water-tight bottom-layer of the sheet and, removing the excess of super absorbent polymer (SAP) powder not attached to the bottom- or under-layer;
   covering at least one surface of the absorbent layer with a layer of diffusing material, wherein at least the edge areas of the sheet are suitably treated or prepared in order to fasten the layer of diffusing material to the under-layer covered with absorbent layer, and
   shaping the water- or fluid-tight bag for collecting or disposing of body fluids or other body wastes by forming an envelope at the desired place of the fluid absorbing sheet, or alternatively attaching a ready-made water- or fluid-tight bag.

8. The method of manufacturing a fluid absorbing sheet according to claim 7, wherein the super absorbent polymer (SAP) is sprayed or showered onto the water-tight bottom-layer simultaneously or after a glue or glue agent is applied.

9. The method of manufacturing a fluid absorbing sheet according to claim 7, wherein the super absorbent polymer (SAP) is laminated to the bottom- or under-layer.

10. A method of using the fluid absorbing sheet according to claim 1 to cover and protect mattresses, stretchers, beds or bed equipment comprising contacting the fluid absorbing sheet according to claim 1 with a mattress, stretcher, bed, or bed equipment.

11. The method according to claim 10, further comprising determining the amount of body fluids or other body wastes collected by said water- or fluid-tight bag.

12. The fluid absorbing sheet according to claim 1, wherein the super absorbent polymer (SAP) powder has a particle size between 15-50 um.

13. A fluid absorbing sheet comprising:
a bottom- or under-layer of water- or fluid-tight material;
a middle layer of super absorbent polymer (SAP); and
an upper layer of diffusing material,
    wherein said super absorbent polymer (SAP) is in a powder form and is attached onto the under-layer, and said upper layer covers the middle layer of super absorbent polymer (SAP) and is attached to the under-layer at least in the edge areas,
    wherein said fluid absorbing sheet further comprises at least one water- or fluid-tight bag for collecting or disposing of body fluids or other body wastes and,
    wherein the thickness of said fluid absorbing sheet is less than 0.70 mm, and further wherein the bottom- or under-layer of the water- or fluid-tight material is a biodegradable bioplastic, wherein the at least one water- or fluid-tight bag is formed at least in part with a fold in the sheet.

14. The fluid absorbing sheet according to claim 13, wherein the at least one water- or fluid-tight bag is configured to be removed from the sheet.

15. The fluid absorbing sheet according to claim 14, wherein the at least one water- or fluid-tight bag is attached to the sheet with a perforated connection.

16. A fluid absorbing sheet comprising:
a bottom- or under-layer of water- or fluid-tight material;
a middle layer of super absorbent polymer (SAP);
an upper layer of diffusing material; and
at least one additional layer of fluid absorbing sheet removably attached to the sheet;
    wherein said super absorbent polymer (SAP) is in a powder form and is attached onto the under-layer, and said upper layer covers the middle layer of super absorbent polymer (SAP) and is attached to the under-layer at least in the edge areas,
    wherein said fluid absorbing sheet further comprises at least one water- or fluid-tight bag for collecting or disposing of body fluids or other body wastes and,
    wherein the thickness of said fluid absorbing sheet is less than 0.70 mm, and further wherein the bottom- or under-layer of the water- or fluid-tight material is a biodegradable bioplastic.

17. The fluid absorbing sheet according to claim 16, wherein the at least one additional layer of fluid absorbing sheet removable attached to the sheet further comprises at least one additional absorbing layer comprising an upper layer of diffusing material, a middle layer of super absorbent polymer (SAP) and a bottom- or under-layer of water- or fluid-tight material, provided and attached onto the sheet at least in the area where the excess or bulk of body fluids is expected.

18. The fluid absorbing sheet according to claim 1, wherein the upper layer of diffusing material has a hydrophilic surface.

19. The fluid absorbing sheet according to claim 13, wherein the sheet is sized and shaped to fit a bed and the at least one water- or fluid-tight bag is removably attached to the sheet and configured to hang from an end of the bed.

20. The fluid absorbing sheet according to claim 13, wherein the super absorbent polymer (SAP) powder has a particle size between 15-50 um.

* * * * *